US00PP35605P2

(12) United States Plant Patent
Postill

(10) Patent No.: US PP35,605 P2
(45) Date of Patent: Jan. 30, 2024

(54) ***PHILADELPHUS* PLANT NAMED 'P1'**

(50) Latin Name: ***Philadelphus* sp.**
Varietal Denomination: P1

(71) Applicant: Alan Postill, Hampshire (GB)

(72) Inventor: Alan Postill, Hampshire (GB)

( * ) Notice: Subject to any disclaimer, the term of this patent is extended or adjusted under 35 U.S.C. 154(b) by 0 days.

(21) Appl. No.: 18/118,353

(22) Filed: Mar. 7, 2023

(51) Int. Cl.
*A01H 5/00* (2018.01)
*A01H 6/48* (2018.01)

(52) U.S. Cl.
USPC ..... Plt./226

(58) Field of Classification Search
USPC ..... Plt./226
See application file for complete search history.

(56) References Cited

PUBLICATIONS

CPVO Register—Application Consulltation version 4.9.14; citaiton for 'P1'. (Retrieved from the Internet on Jun. 23, 2023)(3 pages total).*

* cited by examiner

*Primary Examiner* — Susan McCormick Ewoldt
(74) *Attorney, Agent, or Firm* — Cassandra Bright

(57) ABSTRACT

A new and distinct *Philadelphus* cultivar named 'P1' is disclosed, characterized by a compact habit, and large, white and pink flowers with a strong, pleasant scent. The new variety is a *Philadelphus*, normally used for outdoor ornamental purposes.

2 Drawing Sheets

Figure 1:
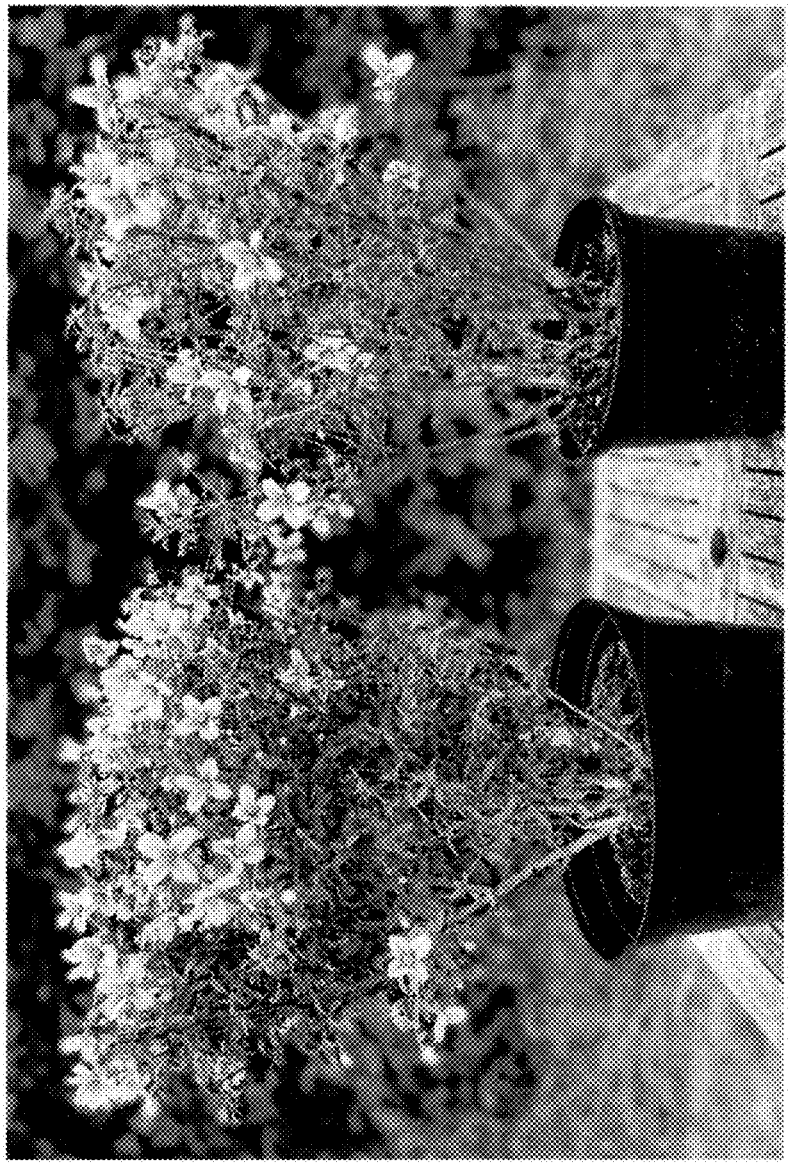

Latin name of the genus and species: *Philadelphus* sp.
Variety denomination: 'P1'.

BACKGROUND OF THE INVENTION

The new *Philadelphus* cultivar is a product of a planned breeding program conducted by the inventor in Hampshire, United Kingdom. The objective of the breeding program was to develop large flowers with a nice, strong scent, and clear white flower color. The open-pollination resulting in this new variety was made during 2014.

The seed parent is the unpatented variety *Philadelphus maculatus* 'Sweet Clare'. The pollen was taken from several unnamed, unpatented proprietary *Philadelphus* seedlings. The new variety was selected in 2018 by the inventor in a group of seedlings resulting from the 2014 crossing, in a nursery in Hampshire, United Kingdom.

Asexual reproduction of the new cultivar was performed by softwood cuttings. This was first performed at the same nursery in Hampshire, United Kingdom in 2018, and has shown that the unique features of this cultivar are stable and reproduced true to type in multiple successive generations.

SUMMARY OF THE INVENTION

The cultivar 'P1' has not been observed under all possible environmental conditions. The phenotype may vary somewhat with variations in environment such as temperature, day length, and light intensity, without, however, any variance in genotype.

The following traits have been repeatedly observed and are determined to be the unique characteristics of 'P1' These characteristics in combination distinguish 'P1' as a new and distinct *Philadelphus* cultivar:

1. Relatively large flowers.
2. Pink and white flowers.

3. Compact size.
4. Floriferous.
5. Strong, pleasant scent.

PARENT COMPARISONS

Plants of the new cultivar 'P1' are similar to plants of the seed parent in most horticultural characteristics; however, plants of the new cultivar 'P1' differ in the following;

1. The new variety is a more compact plant than the seed parent.
2. Flowers of the new variety are outwardly facing; flowers of the seed parent are downward facing.

The exact pollen parent cannot be identified.

COMMERCIAL COMPARISONS

Plants of the new cultivar 'P1' are comparable to the commercial variety *Philadelphus* 'W1', (co-pending, application Ser. No. 18/118,361). The two *Philadelphus* varieties are similar in most horticultural characteristics; however, the new variety 'P1' differs in the following;

1. Petals of the new variety are white with pink, while petals of this comparator are fully white.
2. Petals of this comparator are broader with a rounder tip, and more overlapping than petals of the new variety.
3. Petals of the new variety are not as strongly reflexed back as petals of 'W1'.

Plants of the new cultivar 'P1' are comparable to the commercial variety *Philadelphus* 'Sybille', unpatented. The two *Philadelphus* varieties are similar in most horticultural characteristics; however, the new variety 'P1' differs in the following;

1. Flower color of the new variety is darker, more intense pink, and overall more pink; the flower color of this comparator has only a hint of pale pink in the heart of the flower.

2. Petals of this comparator are broader with a rounder tip, and more overlapping than petals of the new variety.

BRIEF DESCRIPTION OF THE PHOTOGRAPHS

The accompanying photograph in FIG. 1 illustrates in full color two typical flowering plants of 'P1'. Age of the plants photographed is approximately 2 years old from a rooted cutting.

Figure 2:
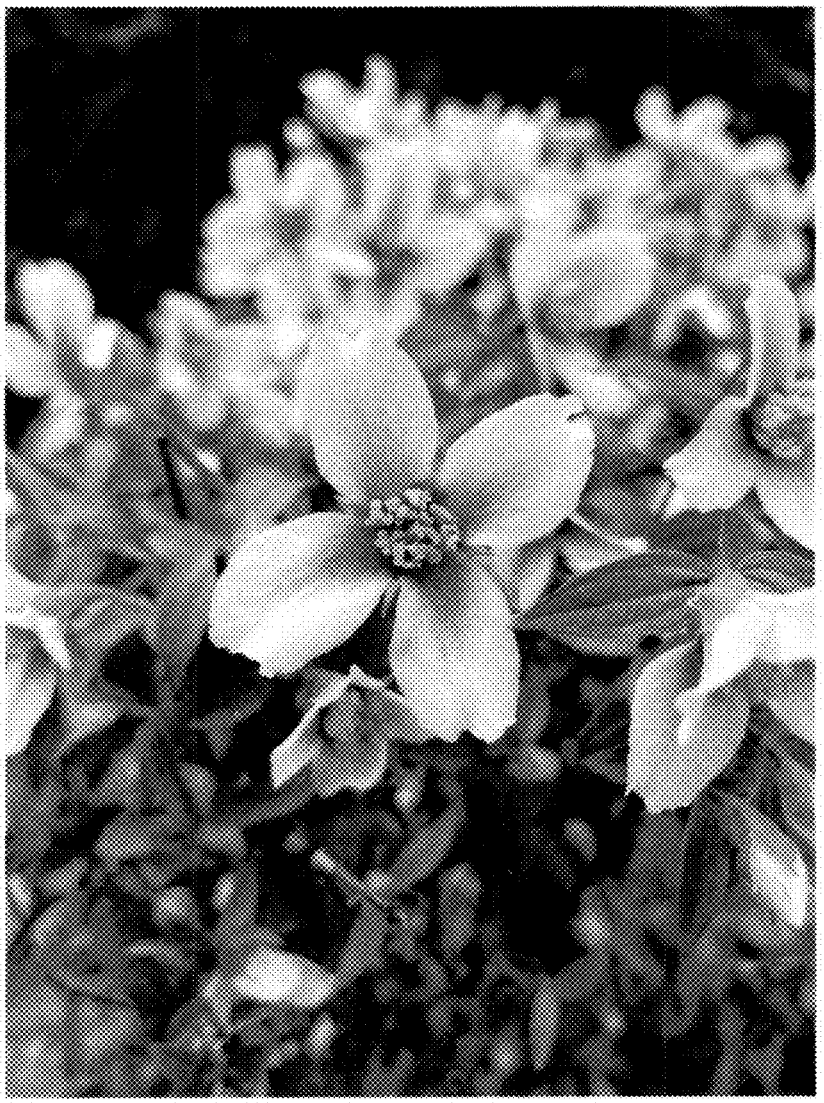

FIG. 2 illustrates a close up view of the flowers.

The photographs were taken using conventional techniques and although colors may appear different from actual colors due to light reflectance it is as accurate as possible by conventional photographic techniques.

DETAILED BOTANICAL DESCRIPTION

In the following description, color references are made to The Royal Horticultural Society Colour Chart 2015 except where general terms of ordinary dictionary significance are used. The following observations and measurements describe 'P1' plants grown outdoors in Waddinxveen, the Netherlands. The growing temperature ranged from approximately 18° C. to 27° C. during the day and from approximately 5° C. to 10° C. during the night. General light conditions are normal sunlight and numerical values represent averages of typical plant types.

Botanical classification: *Philadelphus* sp. 'P1'.

PROPAGATION

Type of propagation typically used: Hardwood cuttings.
Time to initiate roots: 6 weeks in summer.
Time to produce a rooted cutting: 1 year from rooted plug.

PLANT

Age of plant described: 3 years old.
Container size: 23 cm container.
Plant type: Shrub.
Growth habit: Compact.
Plant spread: 95 cm.
Plant height: 84 cm.
Branching habit: Free branching. 5 basal branches.
Length of primary lateral branches: 125 cm.
Diameter of lateral branches: 7 mm.
Quantity of lateral branches: 16.
Stem:
- *Color*.—Young branches: RHS Yellow-Green 145A. Mature branches: RHS Red 59A. Woody branches: RHS Brown 199A.
- *Strength*.—Strong.
- *Length*.—Average range 40 to 70 cm, unpruned.
- *Width*.—Average 5 to 9 mm.

Internode length: Average range 2 cm to 5 cm.

FOLIAGE

Leaf:
- *Arrangement*.—Opposite or sub-opposite.
- *Length*.—Average range 2.5 cm to 3.5 cm. Longest foliage 4.5 cm.
- *Width*.—Average range 1.5 cm to 1.8 cm. Widest foliage 2.3 cm.
- *Shape of blade*.—Ovate to narrow ovate.
- *Apex*.—Acute.
- *Base*.—Tapered.
- *Margin*.—Entire.
- *Texture*.—Glabrous.
- *Color*.—Young foliage upper side: RHS Green 137C. Young foliage under side: RHS Green 137C. Mature foliage upper side: Near RHS Green 137A. Mature foliage under side: Near RHS Green 137A.
- *Venation*.—Pattern: Pinnate. Venation color upper side: RHS Green 137C. Venation color under side: RHS Green 137C.
- *Petiole*.—Length: 3 mm. Diameter: 1.5 mm. Color: RHS Yellow-Green 144B.

FLOWER

Natural flowering season: Late May and June, reblooms in summer.
Flowers per lateral stem: 18 flowers per branch are open. In total around 200 flowers open.
Flowers buds per plant: 16 buds per branch.
Individual flowers:
- *Shape*.—Cruciform.
- *Diameter*.—4.9 cm.
- *Depth*.—2.2 cm.
- *Aspect*.—Outwardly facing.
- *Fragrance*.—Strong, sweet, pleasant.

Petals:
- *Arrangement*.—Cruciform, very slightly overlapping to non-overlapping.
- *Number*.—4.
- *Shape*.—Oblong to obovate.
- *Margin*.—Entire.
- *Apex*.—Rounded. Irregularly notched. Most commonly 1 notch about 6 mm deep. 2 to 4 shallow notches may be present instead.
- *Base*.—Attenuate.
- *Length*.—2 cm.
- *Width*.—1.4 cm.
- *Texture*.—Glabrous all surfaces.
- *Color*.—Upper surface: RHS White 155C and Red-Purple 70B. Under surface: RHS White 155C and Red-Purple 70B.

Bud:
- *Shape*.—Ovate.
- *Length*.—About 12 mm.
- *Diameter*.—About 7 mm.
- *Color*.—RHS White 155C flushed Red-Purple 70B.

Sepals:
- *Quantity per flower*.—4.
- *Arrangement*.—Cruciform.
- *Shape*.—Elliptic.
- *Apex*.—Aristate.
- *Base*.—Fused.
- *Margin*.—Entire.
- *Length*.—1.1 cm.
- *Width*.—0.4 cm.
- *Texture*.—Pubescent.
- *Color*.—Upper: RHS Yellow-Green 144A. Lower: RHS Yellow-Green 144A.

Peduncle:
- *Length*.—About 5 mm.
- *Diameter*.—1 mm.
- *Texture*.—Pubescent.

*Angle*.—Upright.

*Color*.—RHS Yellow-Green 144A.

*Strength*.—Strong.

Pedicel: None.

Petaloids: None.

REPRODUCTIVE ORGANS

Stamens:

*Number*.—About 20.

*Filament length*.—0.9 mm.

*Filament color*.—RHS Yellow-White 158D.

Anthers:

*Shape*.—Linear, basifixed.

*Length*.—1 mm.

*Color*.—RHS Grey-Green 194A.

*Pollen amount*.—Low.

Pistil:

*Number*.—1.

*Length*.—6 mm.

*Style*.—Length: About 4 cm. Color: RHS White 155D with Red-Purple 70B towards base.

Stigma:

*Shape*.—Oblong.

*Length*.—2 mm.

*Color*.—RHS Yellow 4D.

*Ovary color*.—RHS Yellow-Green 144D.

OTHER CHARACTERISTICS

Fruits and seeds: Not observed to date.

Disease/pest resistance: Neither resistance nor susceptibility to normal diseases and pests of *Philadelphus* observed.

Temperature range: Winter hardy to −29° C.

What is claimed is:

1. A new and distinct cultivar of *Philadelphus* plant named 'P1' as herein illustrated and described.

* * * * *